United States Patent
Tan et al.

[11] Patent Number: 5,524,312
[45] Date of Patent: Jun. 11, 1996

[54] ELECTRIC TOOTHBRUSH

[76] Inventors: Kuo-Ching Tan, No.7-3, Alley 1, Lane 54, Ho Ping St., Chung Ho City, Taipei Hsien; Ching-Tsung Hou, 6F, No.25, Lane 102, Ching Li St., Tu Cheng City, Taipei Hsien, both of Taiwan

[21] Appl. No.: 398,817

[22] Filed: Mar. 6, 1995

[51] Int. Cl.⁶ ................................................ A61C 17/34
[52] U.S. Cl. ................................................ 15/22.1
[58] Field of Search ............................ 15/22.1, 22.2, 15/22.4

[56] References Cited

U.S. PATENT DOCUMENTS

| | | | |
|---|---|---|---|
| 4,545,087 | 10/1985 | Nahum | 15/22.1 |
| 5,020,179 | 6/1991 | Scherer | 15/221 |

FOREIGN PATENT DOCUMENTS

| | | | |
|---|---|---|---|
| 0537465 | 4/1993 | European Pat. Off. | 15/22.1 |

*Primary Examiner*—Edward L. Roberts, Jr.
*Attorney, Agent, or Firm*—Morton J. Rosenberg; David I. Klein

[57] ABSTRACT

An electric toothbrush having a circular front chamber and a rectangular rear chamber on the brush head thereof, a first brush holder and a second brush holder respectively mounted in the circular front chamber and the rectangular rear chamber, a transmission rod mounted inside the brush head and reciprocated by a DC motor drive, the transmission rod having a stub rod engaged into a guide groove on the bottom side of the second brush holder, and an upright pin inserted through a side notch on the first brush holder, wherein when the transmission rod is reciprocated by the DC motor drive, the second brush holder is forced to oscillate in the transverse direction, and the first brush holder is driven by the upright pin to move round about its own center.

2 Claims, 4 Drawing Sheets

ELECTRIC TOOTHBRUSH

BACKGROUND OF THE INVENTION

The present invention relates to an electric toothbrushes, and relates more particularly to such an electric toothbrush which has two brush holders, that hold a respective bunch of bristles and are driven to make a circular motion and a reciprocating motion respectively for cleaning the teeth in the most efficient way.

A variety of electric toothbrushes have been disclosed, and have appeared on the market. These automatic toothbrushes commonly use a DC motor drive to move the brush holder through a transmission mechanism. The transmission mechanism can be of any type that oscillates, rotates, or vibrates the brush holder. However, simply driving the brush holder in one fixed course cannot clean the teeth effectively. Furthermore, regular electric toothbrushes are commonly complicated and expensive.

SUMMARY OF THE INVENTION

The present invention has been accomplished to provide an electric toothbrush which eliminates the aforesaid drawbacks. It is one object of the present invention to provide an electric toothbrush which moves the bristles in different directions to effectively clean the teeth. It is another object of the present invention to provide an electric toothbrush which is simple in structure and inexpensive to manufacture.

According to one aspect of thee present invention, the electric toothbrush comprises a first brush holder and a second brush holder, and a transmission rod driven by a DC motor drive to move the first brush holder round about its own center and simultaneously to move the second brush holder back and forth alternatively in the transverse direction.

According to another aspect of the present invention, the transmission rod comprises a driving plate at one end and a coupling portion at an opposite end coupled to the DC motor drive. The driving plate has a stub rod engaged into a bottom guide groove on the second brush holder, and an upright pin inserted through a side notch on the first brush holder. Therefore, when the transmission rod is reciprocated, the first brush holder is rotated on its own center, and the second brush holder is alternatively turned back and forth in the transverse direction.

DETAILED DESCRIPTION OF THE PREFERRED EMBODIMENT

Figure 1:
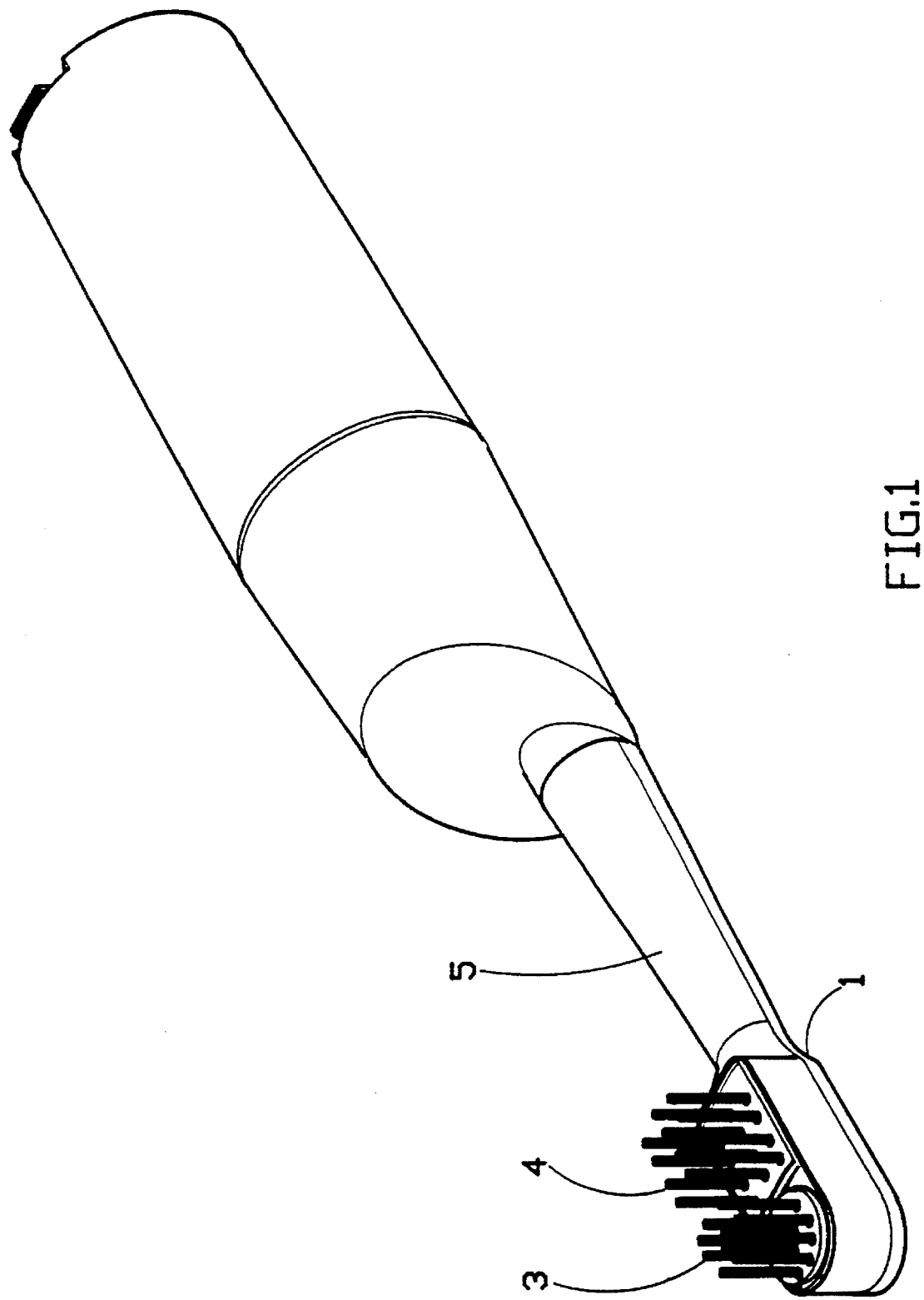
FIG. 1 is an elevational view of an electric toothbrush according to the present invention.
Figure 2:
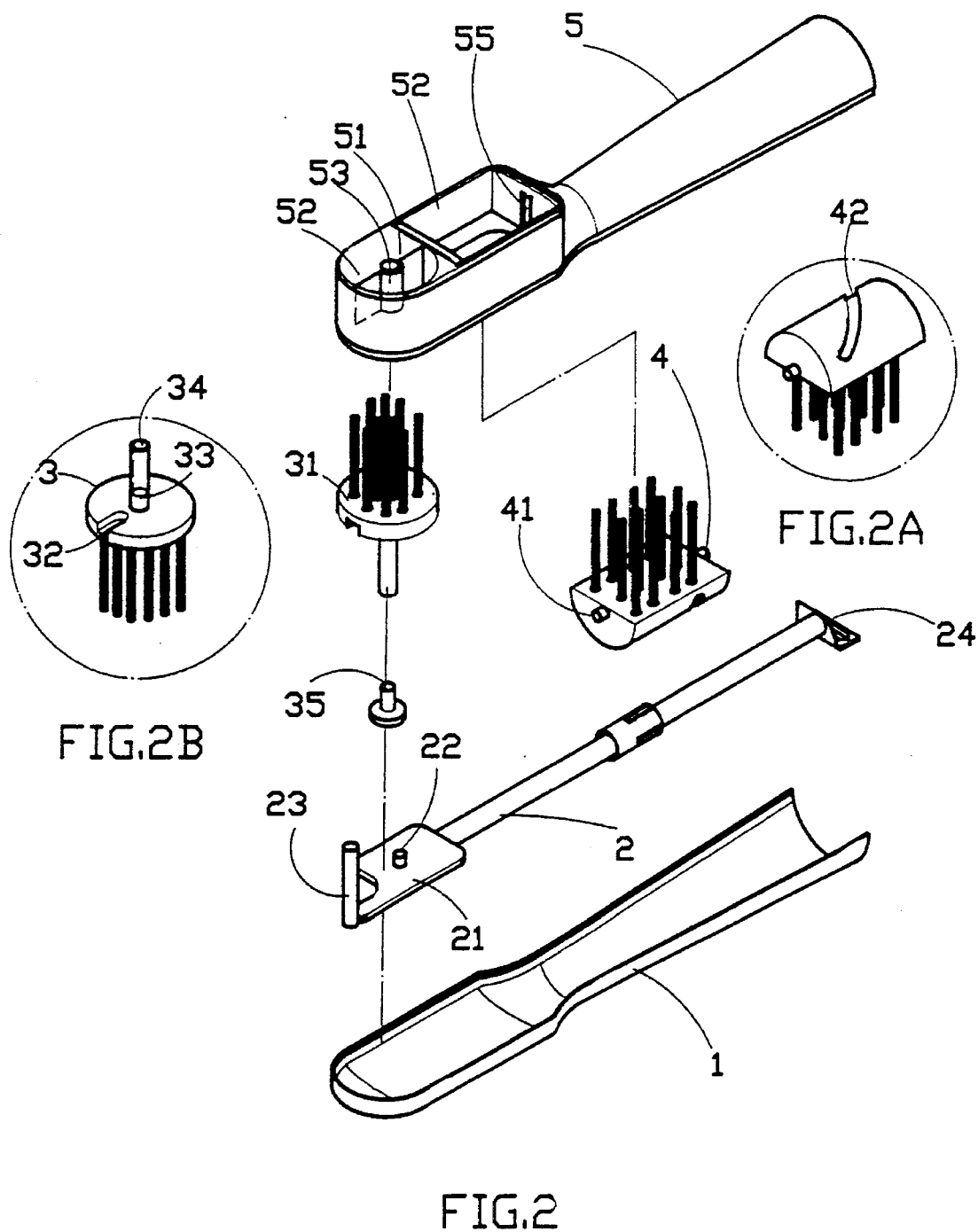
FIG. 2 is an exploded view of the brush head shown in FIG. 1.

Referring to FIGS. 1 and 2, an electric toothbrush in accordance with the present invention is generally comprised of a brush head, which is comprised of a bottom shell 1, a transmission rod 2, a first brush holder 3, a second brush holder 4, and a cover shell 5, a handle 6 connected to the brush head for the holding by the hand of a user, and a DC motor drive 9 (see also FIG. 4) mounted inside the handle 6.

The transmission rod 2 comprises a driving plate 21 at one end and a coupling portion 24 at an opposite end coupled to the output end of the DC motor drive 9. The driving plate 21 has a stub rod 22 at the center, and an upright pin 23 at the front end thereof. The first brush holder 3 comprises a circular base plate 31, which holds a bunch of bristles, a side notch 32 on the base plate 31, an upright rod 33 extended from the center of the bottom side of the base plate 31 and defining a retaining hole 34. The second brush holder 4 has two pivot pins 41 aligned at two opposite ends thereof, and a bottom guide groove 42 angularly directed on the arcuate bottom side thereof. The cover shell 5 comprises a circular front chamber 51, a rectangular rear chamber 52 adjacent to the circular front chamber 51, an upright partition 54 having a semi-cylindrical portion 56 disposed inside the circular front chamber 51, a barrel 53 fixedly secured to the semi-cylindrical portions 56 of partition 54, and two pin holes 55 at two opposite side walls of the rear chamber 52.

Figure 3:
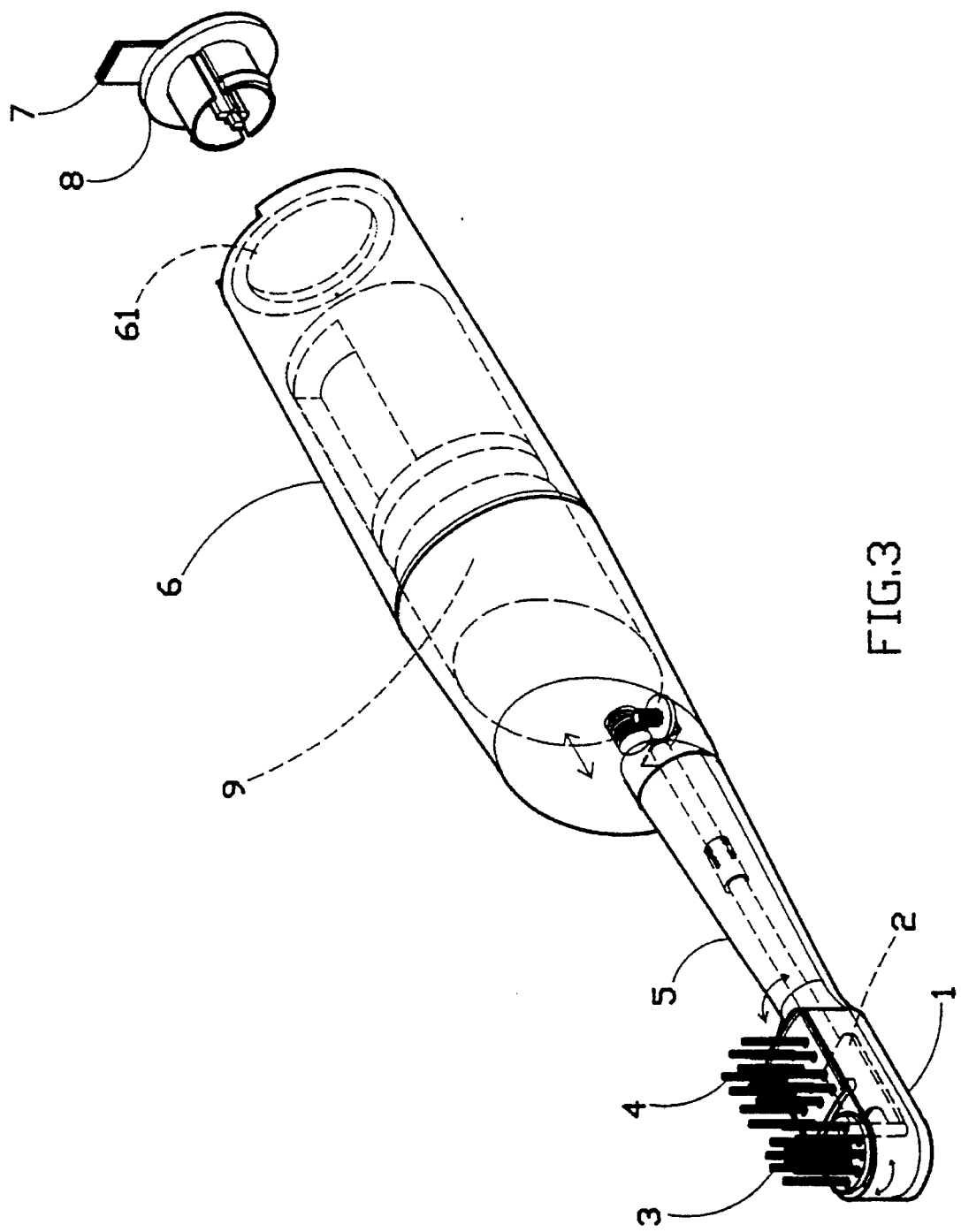
FIG. 3 is a perspective view showing the electric toothbrush operated.
Figure 4:
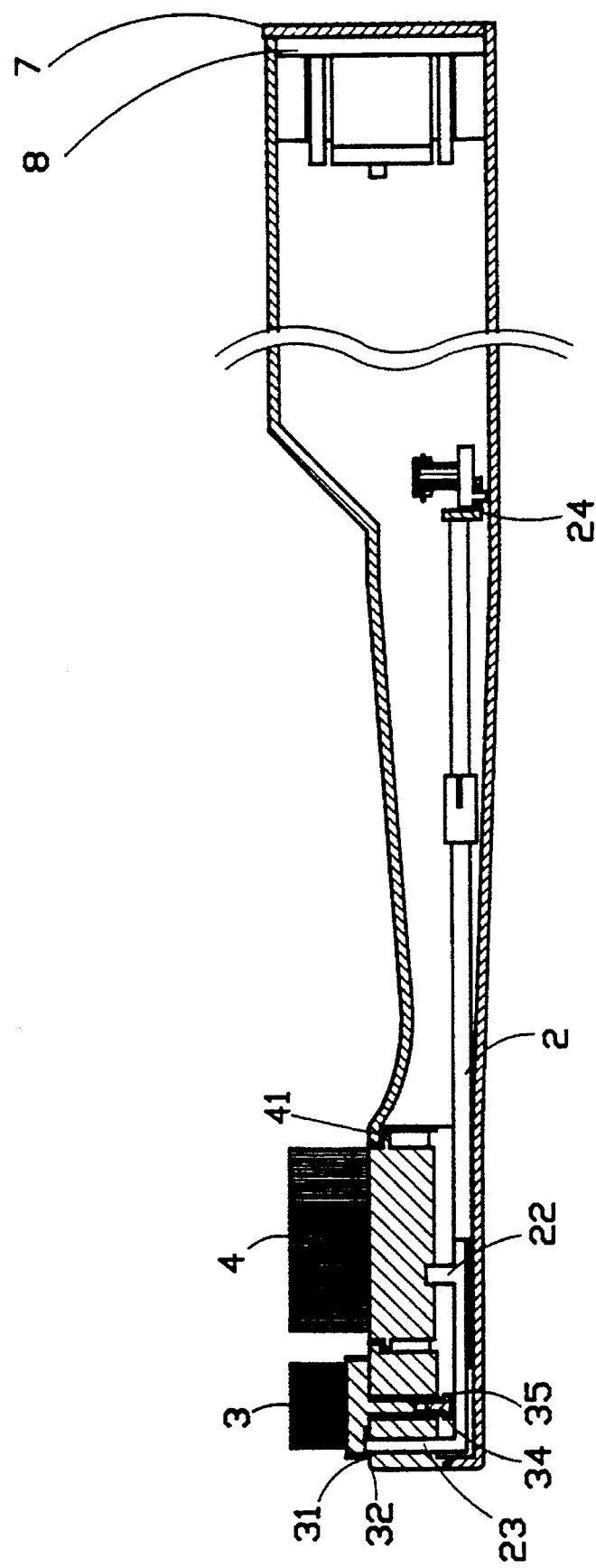
FIG. 4 is a longitudinal view in section of FIG. 1.

Referring to FIGS. 3 and 4 and FIG. 2 again, the first brush holder 3 is loaded in the circular front chamber 51 of the cover shell 5 from the top and secured in place by inserting the upright rod 33 into the barrel 53 and then fastening a fastener 35 to the retaining hole 34 on the upright rod 33. The second brush holder 4 is loaded in the rectangular rear chamber 52 from the bottom and secured in place by inserting the pivot pins 41 into the pin holes 55 respectively. When the transmission rod 2 is placed in the bottom shell 1, the cover shell 5 is fastened to the bottom shell 1, permitting the stub rod 22 to be inserted into the bottom guide groove 42 on the second brush holder 4 and the upright pin 23 to be inserted through the side notch 32 on the first brush holder 3. When the DC motor drive 9 is started to reciprocate the transmission rod 2, the second brush holder 4 is forced to oscillate in the transverse direction, and the first brush holder 3 is driven by the upright pin 23 to move round about its own center.

Referring to FIG. 3 again, a back cover switch 7 is mounted with a gasket 8 and fastened to the brush handle 6 to close the rear opening 61 of the brush handle 6 and to control the operation of the DC motor drive 9.

While only one embodiment of the present invention has been shown and described, it will be understood that various modifications and changes could be made without departing from the spirit and scope of the invention.

What is claimed is:

1. An electric toothbrush comprising a handle, a brush head fastened to one end of said handle to hold a bristle unit, a DC motor drive mounted inside said handle and a transmission rod reciprocally driven by said DC motor drive to move said bristle unit in cleaning the teeth, wherein:

said brush head comprises a bottom shell and a cover shell coupled to said bottom shell to retain said transmission rod therebetween, said cover shell comprising a circular front chamber, a rectangular rear chamber adjacent to said circular front chamber, an upright partition having semi-cylindrical portion disposed inside said circular front chamber, a barrel fixedly secured to said semi-cylindrical portion of said partition, and two pin holes in each of two opposite side walls inside said rectangular rear chamber;

said bristle unit being comprised of a first brush holder and a second brush holder, said first brush holder including a circular base plate mounted within the circular front chamber of said cover shell and supported above said partition to hold a bunch of bristles, said base plate having a side notch formed therein and being secured in place by a fastener, said second brush holder holding a bunch of bristles and having a pair of opposing ends, said second brush holder having a pivot pin extending from each of said opposing ends, each of said pivot pins being respectively inserted into the pin holes formed in said rectangular rear chamber side walls, said second brush holder having an arcuate bottom surface with an angularly directed bottom guide groove formed therein; and said transmission rod having a driving plate formed on one end thereof and a coupling portion formed on an opposing end and coupled to said DC motor drive to provide reciprocation of said transmission rod, said driving plate having a stub rod extending therefrom for engagement within said bottom guide groove for rotating said second brush holder about said pivot pins responsive to said reciprocation of said transmission rod, said driving plate having an upright pin extending therefrom for engagement within said side notch of said base plate for rotating said first brush holder about said upright rod responsive to said reciprocation of said transmission rod.

2. The electric toothbrush of claim 1 wherein said handle has a rear opening covered with a cover switch for controlling the operation of said DC motor drive, said cover switch having a gasket for sealing said rear opening of said handle.

* * * * *